(12) United States Patent
Sekifuji et al.

(10) Patent No.: US 10,881,758 B2
(45) Date of Patent: Jan. 5, 2021

(54) WATER-PERMEABILITY-IMPARTING AGENT, WATER-PERMEABLE FIBER, NON-WOVEN FABRIC, AND WATER-ABSORBING ARTICLE

(71) Applicant: SANYO CHEMICAL INDUSTRIES, LTD., Kyoto (JP)

(72) Inventors: Masayoshi Sekifuji, Kyoto (JP); Yoshiyuki Wakahara, Kyoto (JP)

(73) Assignee: SANYO CHEMICAL INDUSTRIES, LTD., Kyoto (JP)

( * ) Notice: Subject to any disclaimer, the term of this patent is extended or adjusted under 35 U.S.C. 154(b) by 663 days.

(21) Appl. No.: 15/544,979

(22) PCT Filed: Jan. 25, 2016

(86) PCT No.: PCT/JP2016/051967
§ 371 (c)(1),
(2) Date: Jul. 20, 2017

(87) PCT Pub. No.: WO2016/121673
PCT Pub. Date: Aug. 4, 2016

(65) Prior Publication Data
US 2018/0000979 A1 Jan. 4, 2018

(30) Foreign Application Priority Data
Jan. 26, 2015 (JP) ................... 2015-012036

(51) Int. Cl.
| | | |
|---|---|---|
| *A61L 15/42* | (2006.01) | |
| *D06M 13/17* | (2006.01) | |
| *D06M 13/256* | (2006.01) | |
| *D06M 15/53* | (2006.01) | |
| *A61F 13/511* | (2006.01) | |
| *A61F 13/49* | (2006.01) | |
| *A61F 13/15* | (2006.01) | |
| *D04H 1/42* | (2012.01) | |
| *A61L 15/48* | (2006.01) | |
| *A61L 15/20* | (2006.01) | |
| *A61L 15/26* | (2006.01) | |
| *D04H 1/4291* | (2012.01) | |
| *D04H 1/4334* | (2012.01) | |
| *D04H 1/435* | (2012.01) | |
| *D06M 13/188* | (2006.01) | |

(52) U.S. Cl.
CPC .............. *A61L 15/42* (2013.01); *A61F 13/15* (2013.01); *A61F 13/49* (2013.01); *A61F 13/511* (2013.01); *A61F 13/51121* (2013.01); *A61L 15/20* (2013.01); *A61L 15/26* (2013.01); *A61L 15/48* (2013.01); *D04H 1/42* (2013.01); *D04H 1/4291* (2013.01); *D04H 1/435* (2013.01); *D04H 1/4334* (2013.01); *D06M 13/17* (2013.01); *D06M 13/188* (2013.01); *D06M 13/256* (2013.01); *D06M 15/53* (2013.01)

(58) Field of Classification Search
CPC .... D06M 15/53; D06M 13/224; D06M 13/17; D06M 13/188; D06M 13/256; D06M 101/20; D06M 101/32; D06M 13/165; D06M 13/192; D06M 7/00; A61L 15/20; A61L 15/26; A61F 13/15; A61F 13/49; A61F 13/511; A61F 13/51121; A61F 5/44; D04H 1/4291; D04H 1/42; D04H 1/4334; D04H 1/435; D21H 17/14; D21H 13/14; D21H 13/24; C10M 2207/14; C10M 2207/142; C10M 2207/34; C10M 2207/40; C10M 2209/104; C10M 2209/105; C10M 2209/106; C10M 2209/109; Y10T 156/10; Y10T 428/2907; Y10T 428/2933
USPC ......... 428/357, 361, 378; 8/115.6; 252/8.84, 252/79, 8.81, 8.86; 554/227; 508/485; 427/394; 57/250, 231, 258, 292; 156/60, 156/332; 524/315, 311, 321
See application file for complete search history.

(56) References Cited

U.S. PATENT DOCUMENTS

2003/0027729 A1* 2/2003 Kaimai ................ C10M 169/04
508/280

FOREIGN PATENT DOCUMENTS

| CN | 1948605 | 4/2007 |
|---|---|---|
| CN | 101033582 | 9/2007 |
| JP | 4-73271 | 3/1992 |
| JP | 4-82961 | 3/1992 |
| JP | 4-240266 | 8/1992 |

(Continued)

OTHER PUBLICATIONS

Agricultural products Organic Chemical Industry, Apr. 1979.
International Search Report dated Apr. 19, 2016 in International (PCT) Application No. PCT/JP2016/051967.

*Primary Examiner* — Camie S Thompson
(74) *Attorney, Agent, or Firm* — Wenderoth, Lind & Ponack, L.L.P.

(57) ABSTRACT

A water permeability-imparting agent containing an alkylene oxide adduct (A) of a polyvalent active hydrogen compound represented by Formula (1):

$$R-[O(A^1O)_m-(CH_2CH_2O)_n-H]_l \quad (1)$$

wherein R represents a residue, after removal of all active hydrogen, of the polyvalent active hydrogen compound; $A^1O$ represents a C2 to C4 alkyleneoxy group; m represents an average addition mole number of $A^1O$ and is a number of 4 to 50; n represents an average addition mole number of $CH_2CH_2O$; and l represents a valence and is an integer of 3 to 6, and an average addition mole number ratio between $A^1O$ and $CH_2CH_2O$ in Formula (1), n/m, is 0 to 0.5.

11 Claims, No Drawings

(56) References Cited

FOREIGN PATENT DOCUMENTS

| | | |
|---|---|---|
| JP | 11-152683 | 6/1999 |
| JP | 2000-265371 | 9/2000 |
| JP | 2001-288682 | 10/2001 |
| JP | 2002-88651 | 3/2002 |
| JP | 2004-324025 | 11/2004 |
| JP | 2007-107131 | 4/2007 |
| JP | 2012-102424 | 5/2012 |
| JP | 2014-079561 | 5/2014 |

* cited by examiner

WATER-PERMEABILITY-IMPARTING AGENT, WATER-PERMEABLE FIBER, NON-WOVEN FABRIC, AND WATER-ABSORBING ARTICLE

TECHNICAL FIELD

The present invention relates to a water permeability-imparting agent suitable for hydrophobic fibers used in the topsheet (surface material) of an absorbing article such as a disposable diaper or a sanitary product. In particular, the present invention relates to a water permeability-imparting agent that improves initial water permeability and repetition water permeability to aqueous liquid (e.g., urine, bodily fluid) passing through the topsheet, as well as the performance of preventing urine and bodily fluid, once absorbed, from flowing back from the topsheet to the wearer, in other words, rewet prevention performance.

BACKGROUND ART

Absorbing articles such as disposable diapers or sanitary products are generally composed of an absorbent made of cotton-like pulp, a superabsorbent polymeric material, or the like disposed between a liquid-permeable topsheet and a liquid-impermeable backsheet. Urine and bodily fluid are absorbed into the absorbent through the topsheet. To prevent discomfort at this time, it is required that urine and bodily fluid are completely absorbed in a very short time, and that less urine and bodily fluid flow back to the surface of the topsheet from the absorbent. Additionally, water permeable materials such as the topsheet are required to have durability because if the treatment agent on the topsheet flows out to cause a sudden drop in the water permeability after only one or two absorptions of urine or bodily fluid, the disposable diaper or sanitary product disadvantageously needs to be more frequently replaced.

Patent Literature 1, for example, proposes a treatment agent for the production of non-woven fabrics, containing alkyl phosphate and polyether-modified silicone. Patent Literature 2 proposes a hydrophilicity-imparting treatment agent for polyester synthetic fiber products, containing a mixture of a starch derivative and/or a cellulose derivative and a water-soluble ethylenically unsaturated monomer.

CITATION LIST

Patent Literature

Patent Literature 1: JP H04-82961 A
Patent Literature 2: JP 2002-88651 A

SUMMARY OF INVENTION

Technical Problem

In recent years, however, there has been a growing demand for improvement in properties of absorbents used in disposable diapers, sanitary products, and the like that repeatedly absorb aqueous liquid such as urine or bodily fluid. Also, there has been a demand for an increase in the absorption amount. The topsheets made of fibers treated with the treating agent of Patent Literature 1 or 2 are thus insufficient in initial water permeability, repetition water permeability, and rewet prevention performance.

The present invention aims to provide a water permeability-imparting agent capable of providing a topsheet of a water-absorbing article which, even after repeated absorptions of aqueous liquid such as urine or bodily fluid, smoothly absorbs aqueous liquid with less decrease in absorption, and which prevents aqueous liquid, once absorbed, from flowing back to the wearer from the topsheet.

Solution to Problem

After intensive studies to solve the above problems, the present inventors arrived at the invention described below.

The present invention relates to a water permeability-imparting agent containing: an alkylene oxide adduct (A) of a polyvalent active hydrogen compound represented by Formula (1):

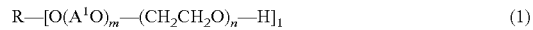

$$R\text{—}[O(A^1O)_m\text{—}(CH_2CH_2O)_n\text{—}H]_l \quad (1)$$

wherein R represents a residue, after removal of all active hydrogen, of the polyvalent active hydrogen compound; $A^1O$ represents a C2 to C4 alkyleneoxy group; m represents an average addition mole number of $A^1O$ and is a number of 4 to 50; n represents an average addition mole number of $CH_2CH_2O$; and l represents a valence and is an integer of 3 to 6, an average addition mole number ratio between $A^1O$ and $CH_2CH_2O$ in Formula (1), n/m, being 0 to 0.5.

The present invention also relates to water-permeable fibers containing hydrophobic fibers and a nonvolatile component of the water permeability-imparting agent attached thereto, a non-woven fabric containing the water-permeable fibers, and a water-absorbing article containing a surface material containing the non-woven fabric.

Advantageous Effects of Invention

The non-woven fabric containing the water-permeable fibers to which has been attached the water permeability-imparting agent of the present invention is excellent in initial water permeability, repetition water permeability, and rewet prevention performance.

DESCRIPTION OF EMBODIMENTS

From the standpoint of improving the repetition water permeability, the water permeability-imparting agent of the present invention contains an alkylene oxide adduct (A) of a polyvalent active hydrogen compound represented by Formula (1) below.

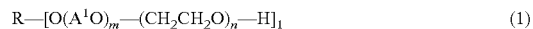

$$R\text{—}[O(A^1O)_m\text{—}(CH_2CH_2O)_n\text{—}H]_l \quad (1)$$

If the water permeability-imparting agent does not contain (A), the non-woven fabric containing the water-permeable fibers to which has been attached the water permeability-imparting agent will have a low repetition water permeability.

In Formula (1) above, R represents the residue, after removal of all active hydrogen, of the polyvalent active hydrogen compound. In Formula (1), l represents a valence, and is an integer of 3 to 6. Examples of the polyvalent active hydrogen compound include trihydric to hexahydric polyols, trivalent to hexavalent polycarboxylic acids, and trivalent to hexavalent polyamines.

Among trihydric to hexahydric polyols, examples of trihydric polyols include glycerol, 1,2,3-butanetriol, 1,2,4-butanetriol, 1,2,3-pentanetriol, 1,2,4-pentanetriol, 2-methyl-1,2,3-propanetriol, 2-methyl-2,3,4-butanetriol, 2-ethyl-1,2,3-butanetriol, 2,3,4-pentanetriol, 3-methylpentane-1,3,5- triol, 2,4-dimethyl-2,3,4-pentanetriol, 2,3,4-hexanetriol, 4-propyl-3,4,5-heptanetriol, 1,3,5-cyclohexanetriol, pentamethyl glycerol, trimethylolethane, trimethylolpropane, castor oil, and hardened castor oil.

Examples of tetrahydric polyols include 1,2,3,4-butanetetraol, pentaerythritol, diglycerol, sorbitan, ribose, arabinose, xylose, and lixose.

Examples of pentahydric polyols include triglycerol, arabitol, xylitol, glucose, fructose, galactose, mannose, allose, gulose, idose, talose, and quercitol.

Examples of hexahydric polyols include dipentaerythritol, sorbitol, galactitol, mannitol, allitol, iditol, talitol, and inositol.

Examples of the trihydric to hexahydric polyols also include animal and vegetable fats and oils other than castor oil and hardened castor oil.

The trihydric to hexahydric polyols may be saccharides. Examples of saccharides include monosaccharides.

Examples of the fatty acid include C8 to C24 aliphatic carboxylic acids [aliphatic saturated carboxylic acids (e.g., caplyric acid, 2-ethylhexanoic acid, pelargonic acid, capric acid, lauric acid, tridecanoic acid, isotridecanoic acid, myristic acid, palmitic acid, stearic acid, and isostearic acid), and aliphatic unsaturated carboxylic acids (e.g., oleic acid, linoleic acid, linolenic acid, ricinoleic acid, castor oil fatty acid, and hardened castor oil fatty acid)].

When R in Formula (1) is the residue, after removal of all active hydrogen, of an alkylene oxide adduct of an ester of a trihydric to hexahydric polyol and a fatty acid, the alkylene oxide adduct (A) of a polyvalent active hydrogen compound represented by Formula (1) preferably has a degree of esterification of 50% or less.

The degree of esterification in the present invention is calculated by Equation (1) below based on the integral areas of mono-, di-, and tri-esters determined by gel permeation chromatography (GPC).

$$\text{Degree of esterification}(\%) = \frac{(\text{Integral area of monoester}) + 2 \times (\text{Integral area of diester})}{3 \times \begin{pmatrix} \text{Integral area of monoester} + \\ \text{Integral area of diester} + \text{Integral area of triester} \end{pmatrix}} \times 100 \quad \text{Equation (1)}$$

From the standpoint of balancing the repetition water permeability and the rewet prevention performance, preferred among these polyols are glycerol, trimethylolpropane, castor oil, hardened castor oil, pentaerythritol, sorbitan, and sorbitol, with trimethylolpropane and pentaerythritol being more preferred.

Among trivalent to hexavalent polycarboxylic acids, examples of trivalent carboxylic acids include 1,2,3-propanetricarboxylic acid, 1,2,4-butanetricarboxylic acid, 1,3,5-cyclohexanetricarboxylic acid, trimer acid (C18 unsaturated carboxylic acid trimer), and trimellitic acid.

Examples of tetravalent carboxylic acids include ethylenetetracarboxylic acid, cyclopentanetetracarboxylic acid, naphthalene-1,4,5,8-tetracarboxylic acid, and butane-1,2,3,4-tetracarboxylic acid.

Examples of pentavalent carboxylic acids include 1,2,3,4,5-cyclohexanepentacarboxylic acid, benzenepentacarboxylic acid, and 1,2,4,5,8-naphthalenepentacarboxylic acid.

Examples of hexavalent carboxylic acid include cyclohexanehexacarboxylic acid, benzenehexacarboxylic acid, and 1,2,3,4,5,7-naphthalenehexacarboxylic acid.

Among trivalent to hexavalent polyamines, examples of trivalent amines include 1,2,3-propanetriamine, hexamethylenetriamine, 1,3,5-benzenetriamine, and melamine.

Examples of tetravalent amines include butane-1,1,4,4-tetraamine, triethylenetetramine, and pyrimidine-2,4,5,6-tetraamine.

The polyvalent active hydrogen compound may contain in the compound at least two active hydrogen groups selected from the group consisting of a carboxy group, a hydroxy group, and an amino group. Examples of the compound containing two or more active hydrogen groups include citric acid, glyceric acid, and amino acids (e.g., lithin, arginine, serine, threonine, tyrosine, aspartic acid, and glutamic acid).

The polyvalent active hydrogen compound may be a partial ester formed from a trihydric to hexahydric polyol and a fatty acid.

Examples of the trihydric to hexahydric polyol include the above compounds.

GPC is conducted under the conditions below.

Device: HLC-8220GPC [available from Tosoh Corporation]

GPC column

Guard column: TSKguardcolumn SuperH-L (4.6 mm I.D.×15 cm)

Separation column: TSKgel SuperH2000 (6 mm I.D.×15 cm)+TSKgel SuperH3000 (6 mm I.D.×15 cm)+TSKgel SuperH4000 (6 mm I.D.×15 cm)

Detector: RI detector

Fluid medium: Tetrahydrofuran

Flow rate: 0.6 mL/min

Column temperature: 40° C.

Sample concentration: 0.25% by weight

Sample amount: 10 µL

From the standpoint of the hydrophilicity and durability of the water permeability-imparting agent, preferred among the above polyvalent active hydrogen compounds are trimethylolpropane, pentaerythritol, 1,2,3-propanetricarboxylic acid, and glutamic acid.

In Formula (1), $A^1O$ represents a C2 to C4 alkyleneoxy group. Specifically, $A^1O$ is an ethyleneoxy group (hereinafter simply an "EO"), a propyleneoxy group (hereinafter simply a "PO"), or a butyleneoxy group (hereinafter simply a "BO"). The PO may be linear or branched. Examples of the BO include 1,2-, 2,3-, 1,3-, 1,4-butyleneoxy groups and an isobutylene group. As $A^1O$, one or two or more alkyleneoxy groups may be used in combination.

In Formula (1), m is the average addition mole number of $A^1O$ per polyalkyleneoxy chain in the branched structure. From the standpoint of the handleability, m is a number of 4 to 50, preferably 8 to 40, more preferably 12 to 30. In Formula (1), m is not necessarily an integer, and may be a decimal.

$A^1O$ is preferably a C3 or C4 alkyleneoxy group. Specifically, $A^1O$ is preferably a PO or a BO, more preferably a PO.

When two or more alkyleneoxy groups are included in $A^1O$, the EO, PO, and BO in $A^1O$ may be added in a random or block fashion. When an EO and at least one of a PO and a BO are included in $A^1O$, preferably an EO and at least one of a PO and a BO are added in a random fashion, more preferably a PO and an EO are added in a random fashion.

The EO addition mole content in $A^1O$ is in the range of 0 to 0.5. The EO addition mole content can be calculated by Equation (2) below.

$$\text{EO addition mole content} = \frac{\text{EO addition mole number in } A^1O}{(EO+PO+BO)\text{addition mole number in } A^1O} \quad \text{Equation (2)}$$

In Formula (1), $CH_2CH_2O$ represents an ethyleneoxy group (EO).

In Formula (1), n is the average addition mole number of $CH_2CH_2O$ per polyalkyleneoxy chain in the branched structure. From the standpoint of improving the repetition water permeability, n is preferably a number of 0 to 15, more preferably 2 to 12, particularly preferably 4 to 9. In Formula (1), n is not necessarily an integer, and may be a decimal.

In Formula (1), $A^1O$ and $CH_2CH_2O$ in the polyalkyleneoxy chain are preferably added in a block fashion. When an EO and at least one of a PO and a BO are included in $A^1O$, it is preferred that $CH_2CH_2O$ is added in a block fashion to $A^1O$ in which an EO and at least one of a PO and a BO are added in a random fashion, and it is more preferred that $CH_2CH_2O$ is added in a block fashion to $A^1O$ in which a PO and an EO are added in a random fashion.

In the polyalkyleneoxy chain in Formula (1), either $A^1O$ or $CH_2CH_2O$ may be positioned at the terminal. From the standpoint of the hydrophilicity and durability of the water permeability-imparting agent, it is preferred that $CH_2CH_2O$ is positioned at the terminal of the polyalkyleneoxy branch chain.

From the standpoint of the repetition water permeability, the average addition mole number ratio between $A^1O$ and $CH_2CH_2O$, n/m, is 0 to 0.5. Preferably n/m is 0.02 to 0.3, more preferably 0.04 to 0.1.

If the average addition mole number ratio between $A^1O$ and $CH_2CH_2O$, n/m, is more than 0.5, the hydrophilicity is high, resulting in low repetition water permeability. Additionally, if the average addition mole number ratio between $A^1O$ and $CH_2CH_2O$, n/m, is more than 0.5, also the rewet prevention performance tends to be low.

The average addition mole number ratio between $A^1O$ and $CH_2CH_2O$ is calculated by theoretical calculation.

The average addition mole number of the alkylene oxide adduct (A) of a polyvalent active hydrogen compound represented by Formula (1) in the present invention can be determined by gel permeation chromatography (GPC).

GPC is conducted under the following conditions.

Device: HLC-8220GPC [available from Tosoh Corporation]

GPC column

Guard column: TSKguardcolumn SuperH-L (4.6 mm I.D.×15 cm)

Separation column: TSKgel SuperH2000 (6 mm I.D.×15 cm)+TSKgel SuperH3000 (6 mm I.D.×15 cm)+TSKgel SuperH4000 (6 mm I.D.×15 cm)

Detector: RI detector

Fluid medium: Tetrahydrofuran

Flow rate: 0.6 mL/min

Column temperature: 40° C.

Sample concentration: 0.25% by weight

Sample amount: 10 μL

In the water permeability-imparting agent of the present invention, examples of the alkylene oxide adduct (A) of a polyvalent active hydrogen compound represented by Formula (1) include a pentaerythritol PO 120 mol adduct (m=30, n=0, n/m=0, l=4), a pentaerythritol BO 60 mol adduct (m=15, n=0, n/m=0, l=4), a pentaerythritol PO 120 mol EO 10 mol block adduct (m=30, n=2.5, n/m=0.083, l=4), a pentaerythritol BO 80 mol EO 12 mol block adduct (m=20, n=3, n/m=0.15, l=4), a trimethylolpropane PO 60 mol adduct (m=20, n=0, n/m=0, l=3), a trimethylolpropane PO 70 mol EO 20 mol block adduct (m=23.3, n=6.7, n/m=0.28, l=3), a trimethylolpropane PO 60 mol EO 6 mol random adduct EO 6 mol block adduct (m=22, n=2, n/m=0.091, l=3), a trimethylolpropane PO 70 mol EO 10 mol random adduct EO 10 mol block adduct (m=26.7, n=3.3, n/m=0.12, l=3), a 1,2,3-propanetricarboxylic acid PO 90 mol EO 3 mol block ester compound (m=30, n=1, n/m=0.033, l=3), and an ester compound (m=24.7, n=3.3, n/m=0.13, l=3) of glutamic acid of a N-PO 6 mol EO 2 mol block adduct and a di-PO 34 mol EO 4 mol block adduct.

In particular, from the standpoint of the hydrophilicity, rewet prevention performance, and durability of the water permeability-imparting agent, preferred are a pentaerythritol PO 120 mol adduct, a pentaerythritol PO 120 mol EO 10 mol block adduct, a trimethylolpropane PO 70 mol EO 20 mol block adduct, and a trimethylolpropane PO 60 mol EO 6 mol random adduct EO 6 mol block adduct.

In the water permeability-imparting agent of the present invention, from the standpoint of the repetition water permeability, the alkylene oxide adduct (A) of a polyvalent active hydrogen compound represented by Formula (1) preferably has a solubility parameter (SP value) of 8.5 to 9.5 $(\text{cal/cm}^3)^{1/2}$, more preferably 8.5 to 9.1 $(\text{cal/cm}^3)^{1/2}$, particularly preferably 8.5 to 8.8 $(\text{cal/cm}^3)^{1/2}$.

The SP value is calculated by the method proposed by Fedors et al. described in the document below. "POLYMER ENGINEERING AND SCIENCE, FEBRUARY, 1974, Vol. 14, No. 2, ROBERT F. FEDORS. (pp.147-154)"

The alkylene oxide adduct (A) of a polyvalent active hydrogen compound represented by Formula (1) preferably has an HLB of 3.5 to 6.5, more preferably 4.0 to 6.0, particularly preferably 4.5 to 5.5, from the standpoint of the repetition water permeability. The HLB is calculated by the following method of calculating HLB (inorganicity/organicity) based on an organic conceptual diagram.

For example, "Nyuka Kayouka no Gijutsu (Technique of Emulsification and Solubilization)" [1976, Kougakutosho Ltd.] discloses a calculation method. The organic value and inorganic value for determining the HLB can be calculated using the inorganic table (1974, reported by Fujita et al.) in "Yuki Gainen Zu-Kiso to Oyo-(Organic Conceptual Diagram—Fundamentals and Applications)" [1984, Sankyo Shuppan Co., Ltd].

From the standpoint of the repetition water permeability, the amount of the alkylene oxide adduct (A) of a polyvalent active hydrogen compound represented by Formula (1) is preferably 10 to 90% by weight, more preferably 20 to 80% by weight, particularly preferably 30 to 70% by weight, based on the weight of the water permeability-imparting agent.

The alkylene oxide adduct (A) of a polyvalent active hydrogen compound represented by Formula (1) can be produced by a known method. For example, it can be produced by addition of an alkylene oxide to any of the above polyols using potassium carbonate or sodium carbonate as a basic catalyst.

The water permeability-imparting agent of the present invention may contain an anionic surfactant (B).

The anionic surfactant (B) significantly improves both the initial water permeability and the repetition water permeability when used in combination with the alkylene oxide adduct (A) of a polyvalent active hydrogen compound represented by Formula (1). In addition, the anionic surfactant (B) can impart good antistaticity and low foamability to fibers for non-woven fabric production. When used alone, the anionic surfactant (B) does not exhibit these effects, especially the improving effect on the repetition water permeability. The mechanism with which the repetition water permeability is significantly improved is unclear, but presumed as follows: In the course of drying the water permeability-imparting agent, the anionic surfactant (B) can control the surface hydrophilicity of the water permeability-imparting agent. The alkyleneoxy groups in the alkylene oxide adduct (A) are presumably drawn to the hydrophilic group of the anionic surfactant (B), so that high hydrophilicity can be obtained.

Specific examples of the anionic surfactant (B) include dialkyl sulfosuccinates, alkyl sulfonates, and alkyl phosphates.

From the standpoint of the initial water permeability, the anionic surfactant (B) is particularly preferably a dialkyl sulfosuccinate. The dialkyl sulfosuccinate preferably has C6 to C18 alkyl groups, more preferably C8 to C16 alkyl groups, particularly preferably C10 to C14 alkyl groups. The alkyl groups may be either linear or branched. The two alkyl groups may be the same as or different from each other. If the alkyl groups have a carbon number of less than 6, the hydrophilicity is too high, leading to low repetition water permeability and low rewet prevention performance. If the alkyl groups have a carbon number of more than 18, the water permeability-imparting agent cannot impart hydrophilicity to non-woven fabric fibers.

The alkyl sulfonate preferably has a C6 to C20 alkyl group, more preferably a C8 to C18 alkyl group, particularly preferably a C10 to C16 alkyl group. The alkyl group may be either linear or branched. If the alkyl group has a carbon number of less than 6, the hydrophilicity is too high, leading to low repetition water permeability and low rewet prevention performance. If the alkyl group has a carbon number of more than 20, the water permeability-imparting agent cannot impart hydrophilicity to non-woven fabric fibers.

Specific examples of the alkyl phosphates include potassium salt of phosphate ester of octyl alcohol, potassium salt of phosphate ester of 2-ethylhexyl alcohol, sodium salt of phosphate ester of decyl alcohol, potassium salt of phosphate ester of isodecyl alcohol, potassium salt of phosphate ester of dodecyl alcohol, sodium salt of phosphate ester of tridecyl alcohol, sodium salt of phosphate ester of isotridecyl alcohol, potassium salt of phosphate ester of tetradecyl alcohol, sodium salt of phosphate ester of hexadecyl alcohol, potassium salt of phosphate ester of an octyl alcohol ethylene oxide (hereinafter simply "EO") 2 mol adduct, sodium salt of phosphate ester of a decyl alcohol EO 3 mol adduct, potassium salt of phosphate ester of a dodecyl alcohol EO 3 mol adduct, potassium salt of phosphate ester of a tridecyl alcohol EO 5 mol adduct, and potassium salt of phosphate ester of an isotridecyl alcohol EO 3 mol adduct. From the standpoint of the initial water permeability, preferred among these salts are potassium salt of phosphate ester of octyl alcohol, sodium salt of phosphate ester of decyl alcohol, potassium salt of phosphate ester of isodecyl alcohol, potassium salt of phosphate ester of an octyl alcohol EO 2 mol adduct, and sodium salt of phosphate ester of a decyl alcohol EO 3 mol adduct.

Two or more anionic surfactants (B) may be used in combination.

From the standpoint of the initial water permeability, preferred as the anionic surfactant (B) are sodium di(2-ethylhexyl) sulfosuccinate, sodium didodecyl sulfosuccinate, and potassium 1-octyl-2-hexadecyl sulfosuccinate.

When the water permeability-imparting agent of the present invention contains the anionic surfactant (B), the amount of the anionic surfactant (B) is preferably 10 to 60% by weight, more preferably 20 to 50% by weight, particularly preferably 30 to 40% by weight, based on the weight of the water permeability-imparting agent.

The water permeability-imparting agent of the present invention may contain a nonionic surfactant (C) other than the alkylene oxide adduct (A) of a polyvalent active hydrogen compound represented by Formula (1).

From the standpoint of improving the initial water permeability, the nonionic surfactant (C) added to the water permeability-imparting agent of the present invention may be, for example, a monohydric alcohol nonionic surfactant. Examples thereof include a polyoxyalkylene alkyl ether (C1). From the standpoint of improving the liquid permeation rate, the nonionic surfactant (C) may be, for example, a polyol nonionic surfactant. Examples thereof include an ester (C2) of a polyol, a polyoxyalkylene adduct, and a fatty acid. From the standpoint of improving the rewet prevention performance, the nonionic surfactant (C) may be, for example, a polyoxyalkylene adduct. Examples thereof include a polyoxyethylene diester (C3).

Two or more nonionic surfactants (C) may be used in combination.

Among the nonionic surfactants (C) added to the water permeability-imparting agent of the present invention, the polyoxyalkylene alkyl ether (C1) is a monohydric alcohol to which has been added an alkylene oxide. The alkyl group of the monohydric alcohol preferably has a carbon number of 1 to 18, more preferably 6 to 16, particularly preferably 8 to 12. If the alkyl group has a carbon number of more than 18, the initial water permeability is low. Here, there may be a distribution of the carbon number of the alkyl group, and two or more monohydric alcohol alkylene oxide adducts may be mixed. Examples of the alkylene oxide include EO, PO, and a block or random polymer thereof. Preferred among them is EO. The addition mole number of the alkylene oxide is preferably 1 to 20, more preferably 2 to 15, particularly preferably 3 to 10.

Among the nonionic surfactants (C) added to the water permeability-imparting agent of the present invention, examples of the ester (C2) of a polyol, a polyoxyalkylene adduct, and a fatty acid include an alkylene oxide adduct (C2-1) of an ester of a polyol and a fatty acid, an ester (C2-2) of a polyol alkylene oxide adduct and a fatty acid, and an ester (C2-3) of a polyoxyalkylene adduct and a fatty acid.

Specific examples of the polyol constituting (C2-1) include C3 to C6 aliphatic polyhydric (trihydric to hexahydric) alcohols (e.g., glycerol, trimethylolpropane, pentaerythritol, sorbitol, and sorbitan).

Specific examples of the fatty acid constituting (C2-1) include C8 to C24 aliphatic carboxylic acids [aliphatic saturated carboxylic acids (e.g., caplyric acid, 2-ethylhexanoic acid, pelargonic acid, capric acid, lauric acid, tridecanoic acid, isotridecanoic acid, myristic acid, palmitic acid, stearic acid, and isostearic acid) and aliphatic unsaturated carboxylic acids (e.g., oleic acid, linoleic acid, linolenic acid, ricinoleic acid, tallow acid, hardened tallow acid, castor oil fatty acid, and hardened castor oil fatty acid)].

Specific examples of the alkylene oxide constituting (C2-1) include C2 to C12 AOs (EO, PO, and BO). One or two or more AOs may be used in combination. When two or more AOs are used in combination, the AOs may be added in a block or random fashion.

Specific examples of (C2-1) include a glycerol tallowate EO 15 mol adduct, a trimethylolpropane trioleate EO 20 mol adduct, a pentaerythritol tetraoleate EO 30 mol adduct, a sorbitan tetraoleate EO 20 mol adduct, a hardened castor oil BO 10 mol adduct, a hardened castor oil EO 25 mol adduct, a castor oil EO 43 mol adduct, a hardened castor oil EO 43 mol adduct, and an EO 25 mol adduct of an ester of glycerol and castor oil fatty acid.

In particular, from the standpoint of the repetition water permeability, a hardened castor oil EO 43 mol adduct is preferred.

Specific examples of the polyol constituting (C2-2) include C3 to C6 aliphatic polyhydric (trihydric to hexahydric) alcohols (e.g., glycerol, trimethylolpropane, pentaerythritol, sorbitol, and sorbitan).

Specific examples of the alkylene oxide constituting (C2-2) include C2 to C12 AOs (EO, PO, and BO). One or two or more AOs may be used in combination. When two or more AOs are used in combination, the AOs may be added in a block or random fashion.

Specific examples of the fatty acid constituting (C2-2) include C8 to C24 aliphatic carboxylic acid [aliphatic saturated carboxylic acids (caplyric acid, 2-ethylhexanoic acid, pelargonic acid, capric acid, lauric acid, tridecanoic acid, isotridecanoic acid, myristic acid, palmitic acid, stearic acid, and isostearic acid) and aliphatic unsaturated carboxylic acids (oleic acid, linoleic acid, linolenic acid, ricinoleic acid, tallow acid, hardened tallow acid, castor oil fatty acid, and hardened castor oil fatty acid)].

Specific examples of (C2-2) include stearate of a castor oil EO 43 mol adduct, oleate of a hardened castor oil EO 20 mol adduct (hardened castor oil EO 20 mol adduct trioleate), tallowate of a castor oil EO 25 mol adduct, a polyester (number average molecular weight: 6000) of a hardened castor oil EO 25 mol adduct, maleic acid, and stearic acid, and a polyester (number average molecular weight: 7000) of a hardened castor oil EO 25 mol adduct, sebacic acid, and stearic acid.

From the standpoint of improving the liquid permeability and the repetition water permeability, preferred is a polyester (number average molecular weight: 6000) of a hardened castor oil EO 25 mol adduct, maleic acid, and stearic acid.

Examples of the alkylene oxide constituting (C2-3) include C2 to C12 AOs (EO, PO, and BO). One or two or more AOs may be used in combination. When two or more AOs are used in combination, the AOs may be added in a block or random fashion.

Specific examples of the fatty acid constituting (C2-3) include C8 to C24 aliphatic carboxylic acids [aliphatic saturated carboxylic acids (e.g., caplyric acid, 2-ethylhexanoic acid, pelargonic acid, capric acid, lauric acid, tridecanoic acid, isotridecanoic acid, myristic acid, palmitic acid, stearic acid, and isostearic acid) and aliphatic unsaturated carboxylic acids (e.g., oleic acid, linoleic acid, and linolenic acid)], and animal and vegetable oil [(e.g., coconut oil, palm oil, castor oil, hardened castor oil, tallow, hardened tallow, and lard)] fatty acids.

From the standpoint of improving the rewet prevention performance, preferred as (C2-3) is polyoxyethylene (number average molecular weight: 400) dioleate.

When two or more esters (C2) of a polyol, a polyoxyalkylene adduct, and a fatty acid are used in combination, it is preferred to use two or more esters selected from the group consisting of (C2-2). It is more preferred to use, in combination, hardened castor oil EO 20 mol adduct trioleate and a polyester (number average molecular weight: 6000) of a hardened castor oil EO 25 mol adduct, maleic acid, and stearic acid.

When the water permeability-imparting agent of the present invention contains the nonionic surfactant (C), from the standpoint of improving the initial water permeability and the rewet prevention performance, the amount of nonionic surfactant (C) is preferably 20 to 70% by weight, more preferably 30 to 60% by weight, particularly preferably 40 to 50% by weight, based on the weight of the water permeability-imparting agent.

The water permeability-imparting agent of the present invention may contain an additive (D), if necessary.

Examples of the additive (D) include lubricants such as wax, antioxidants, ultraviolet absorbers, defoamers, preservatives, and perfumes.

The amount of (D) in the water permeability-imparting agent of the present invention is preferably 5% by weight or less, more preferably 0.1 to 1% by weight, based on the weight of the water permeability-imparting agent.

In the water permeability-imparting agent of the present invention, from the standpoint of improving the repetition water permeability and the liquid permeation rate, the weight ratio [(A)/(B)/(C)] between the alkylene oxide adduct (A) of a polyvalent active hydrogen compound represented by Formula (1), the anionic surfactant (B), and the nonionic surfactant (C) is preferably [(10 to 90)/(0 to 40)/(0 to 50)], more preferably [(20 to 80)/(5 to 35)/(10 to 40)], still more preferably [(30 to 70)/(10 to 30)/(20 to 40)], provided that the total weight of (A), (B) and (C) is 100.

The water permeability-imparting agent of the present invention can be obtained by blending the alkylene oxide adduct (A) of a polyvalent active hydrogen compound represented by Formula (1) and if necessary, components such as water, the anionic surfactant (B), and the nonionic surfactant (C), and uniformly mixing them at normal temperature or if necessary with heating (e.g., 30° C. to 70° C.). The order of blending of the components and the blending method are not limited.

The water permeability-imparting agent of the present invention is preferably used for fibers.

The fibers to which has been applied the water permeability-imparting agent of the present invention is preferably used for a non-woven fabric product, particularly preferably the topsheet of an absorbing article such as a disposable diaper or a sanitary product (e.g., sanitary napkins).

The water permeability-imparting agent of the present invention is typically applied in the form of an aqueous emulsion to hydrophobic fibers.

The aqueous emulsion is preferably prepared by diluting the water permeability-imparting agent by adding water (20° C. to 40° C.) to the agent, or by emulsifying the water permeability-imparting agent by adding the agent to water (20° C. to 40° C.)

The concentration of the aqueous emulsion may be any selected concentration. Yet, the concentration is preferably 0.05 to 20% by weight, more preferably 0.1 to 10% by weight.

Attaching the water permeability-imparting agent of the present invention to hydrophobic fibers gives durable water-permeability to the fibers, thus providing the water-permeable fibers of the present invention.

The method of attaching the water permeability-imparting agent to hydrophobic fibers is not limited. A common method, for example, an oiling roll method, an immersion method, or a spraying method can be used in any step such as spinning or drawing.

The amount, in terms of the nonvolatile component, of the water permeability-imparting agent attached to the fibers is preferably 0.05 to 2% by weight, more preferably 0.1 to 2% by weight based on the weight of the fibers.

The hydrophobic fibers used as a material of the water-permeable fibers of the present invention means fibers having a water absorption of 1% by weight or less at a temperature of 25° C. and a relative humidity of 65%.

The hydrophobic fibers are not limited. Common hydrophobic synthetic fibers can be used, such as fibers made of polyolefin, polyester, or polyamide.

Examples of the polyolefin include polyethylene, polypropylene, ethylene vinyl acetate copolymer, ethylene-propylene copolymer, and ethylene-propylene-1-butene copolymer.

Examples of the polyester include polyethylene terephthalate, polybutylene terephthalate, polytrimethylene terephthalate, polyethylene terephthalate-isophthalate, and polyether polyester.

Examples of the polyamide include 6,6-nylon and 6-nylon.

In particular, polyolefin and polyester are preferred as water-absorbing material for diapers.

The water-permeable fibers to which has been applied the water permeability-imparting agent of the present invention is preferably used in the form of a fabric, such as a woven fabric, a knitted fabric, or a non-woven fabric. Fibers mixed by a method such as cotton blending, mixed spinning, fiber blending, mixed knitting, or mixed weaving may be used in the form of a fabric. Preferred among them is a non-woven fabric.

When the water-permeable fibers to which has been applied the water permeability-imparting agent of the present invention is used for a non-woven fabric, staples (short fibers) treated with the water permeability-imparting agent of the present invention may be formed into a fiber laminate by a dry or wet method and then subjected to pressure bonding with a heat roll, fusion by air heating, or fiber entanglement with high-pressure water streams to produce a non-woven fabric. Alternatively, the water permeability-imparting agent of the present invention may be attached to a non-woven fabric formed by a method such as spun-bonding, melt blowing, or a flash spinning.

The water-permeable fibers of the present invention and the non-woven fabric containing the fibers are suitably used for a surface material of a water-absorbing article, in particular a surface material of a hygienic material such as a disposable diaper or a sanitary product (e.g., sanitary napkins).

The water-permeable fibers of the present invention and the non-woven fabric containing the fibers also can be used as a second sheet, a water-absorbing body, an industrial or medical wiper, an absorbing pad, a water-permeable sheet, and the like.

EXAMPLES

Hereinafter, the present invention is described in detail with reference to examples and comparative examples. The present invention, however, is not limited to these examples.

Production Example 1

Production of Pentaerythritol PO 120 mol Adduct (A-1)

A 1-L autoclave equipped with a stirrer, a thermometer, a manometer, a pressure-resistant dropping funnel, and vacuum and nitrogen-introducing lines was charged with 14 parts by weight of pentaerythritol (I) [molecular weight: 136, product name: Pentarit (available from Koei Chemical Co., Ltd.)] and 0.8 parts by weight of potassium hydroxide, and stirring was started. Nitrogen was injected and the temperature was raised to 90° C. Then, the pressure was reduced to 0.005 MPa, and stirring was performed for one hour. Subsequently, the temperature was raised to 130±10° C., and 696 parts by weight of propylene oxide was added dropwise successively while keeping the pressure at 4 to 6.5 kPa. It took one hour to complete the dropwise addition, and two hours for the pressure to be fully reduced. Thereafter, 10 parts by weight of KYOWAAD 600 (available from Kyowa Chemical Industry Co., Ltd.) was added to perform adsorption treatment at 95° C. for one hour, followed by filtration, whereby alkali metal was removed. The contents of the autoclave was cooled to 60° C. and taken out, whereby 700 parts by weight of an alkylene oxide adduct was obtained. This adduct is taken as a pentaerythritol PO 120 mol adduct (A-1).

Production Example 2

Production of Pentaerythritol PO 120 mol EO 10 mol Block Adduct (A-2)

An amount of 600 parts by weight of the pentaerythritol PO 120 mol adduct (A-1) obtained in Production Example 1 was heated to 130±10° C., and 37.2 parts by weight of ethylene oxide was added dropwise successively while keeping the pressure at 4 to 6.5 kPa. It took 0.5 hours to complete the dropwise addition, and 0.5 hours for the pressure to be fully reduced. Thereafter, 10 parts by weight of KYOWAAD 600 (available from Kyowa Chemical Industry Co., Ltd.) was added to perform adsorption treatment at 95° C. for one hour, followed by filtration, whereby alkali metal was removed. The contents of the autoclave was cooled to 60° C. and taken out, whereby 600 parts by weight of an alkylene oxide adduct was obtained. This adduct is taken as a pentaerythritol PO 120 mol EO 10 mol block adduct (A-2).

Production Example 3

Production of Trimethylolpropane PO 70 mol EO 20 mol Block Adduct (A-3)

A 1-L autoclave equipped with a stirrer, a thermometer, a manometer, a pressure-resistant dropping funnel, and vacuum and nitrogen-introducing lines was charged with 13.4 parts by weight of trimethylolpropane (I) [molecular weight: 134, product name: Trimethylolpropane (available from Bayer Chemicals)] and 0.8 parts by weight of potassium hydroxide, and stirring was started. Nitrogen was injected and the temperature was raised to 90° C. Then, the pressure was reduced to 0.005 MPa, and stirring was performed for one hour. Subsequently, the temperature was raised to 130±10° C., and 406 parts by weight of propylene oxide was added dropwise successively while keeping the pressure at 4 to 6.5 kPa. It took one hour to complete the dropwise addition, and two hours for the pressure to be fully reduced. Subsequently, 88 parts by weight ethylene oxide was added dropwise successively. It took 0.5 hours to complete the dropwise addition, and 0.5 hours for the pressure to be fully reduced. Thereafter, 10 parts by weight of KYOWAAD 600 (available from Kyowa Chemical Industry Co., Ltd.) was added to perform adsorption treatment at 95° C. for one hour, followed by filtration, whereby alkali metal was removed. The contents of the autoclave was cooled to 60° C. and taken out, whereby 500 parts by weight of an alkylene oxide adduct was obtained. This adduct is taken as a trimethylolpropane PO 70 mol EO 20 mol block adduct (A-3).

Production Example 4

Production of Trimethylolpropane PO 60 mol EO 6 mol Random Adduct EO 6 mol Block Adduct (A-4)

A 1-L autoclave equipped with a stirrer, a thermometer, a manometer, a pressure-resistant dropping funnel, and vacuum and nitrogen-introducing lines was charged with 13.4 parts by weight of trimethylolpropane (I) [molecular weight: 134, product name: Trimethylolpropane (available from Bayer Chemicals)] and 0.8 parts by weight of potassium hydroxide, and stirring was started. Nitrogen was injected and the temperature was raised to 90° C. Then, the pressure was reduced to 0.005 MPa, and stirring was performed for one hour. Subsequently, the temperature was raised to 130±10° C., and a mixture of 26.4 parts by weight ethylene oxide and 348.6 parts by weight of propylene oxide was added dropwise successively while keeping the pressure at 4 to 6.5 kPa. It took one hour to complete the dropwise addition, and two hours for the pressure to be fully reduced. Subsequently, 26.4 parts by weight of ethylene oxide was added dropwise successively. It took 0.5 hours to complete the dropwise addition, and took 0.5 hours for the pressure to be fully reduced. Thereafter, 10 parts by weight of KYOWAAD 600 (available from Kyowa Chemical Industry Co., Ltd.) was added to perform adsorption treatment at 95° C. for one hour, followed by filtration, whereby alkali metal was removed. The contents of the autoclave was cooled to 60° C. and taken out, whereby 400 parts by weight of an alkylene oxide adduct was obtained. This adduct is taken as a trimethylolpropane PO 60 mol EO 6 mol random adduct EO 6 mol block adduct (A-4).

Production Example 5

Production of Ester Compound of Glutamic Acid of N-PO 6 mol EO 2 mol Block Adduct and di-PO 34 mol EO 4 mol Block Adduct (A-5)

A reaction vessel equipped with a stirrer, a thermometer, and a nitrogen-introducing line was charged with 200 parts by weight of polypropylene glycol (average molecular weight: about 1000) and 15 parts by weight of glutamic acid (reaction mole ratio: polypropylene glycol:glutamic acid=2:1). To the mixture was added p-toluenesulfonic acid as an esterification catalyst in an amount of 0.5% by weight relative to glutamic acid. While blowing nitrogen into the solution, the temperature was raised to 170° C. Esterification was performed at normal pressure while discharging nitrogen from the reaction vessel. The progress of esterification was checked by measuring the acid value. The reaction was continued for eight hours until the acid value reached 1 or less. KYOWAAD 600 (available from Kyowa Chemical Industry Co., Ltd.) in an amount of 10 parts by weight was added to perform adsorption treatment at 95° C. for one hour, followed by filtration, whereby residual catalyst was removed. The contents of the vessel was cooled to 60° C. and taken out, whereby glutamic acid dipolypropylene glycol ester (II) was obtained.

A 1-L autoclave equipped with a stirrer, a thermometer, a manometer, a pressure-resistant dropping funnel, and vacuum and nitrogen-introducing lines was charged with 215 parts by weight of the glutamic acid dipolypropylene glycol ester (II), and stirring was started. Nitrogen was injected and the temperature was raised to 90° C. Then, the pressure was reduced to 0.005 MPa, and stirring was performed for one hour. Subsequently, the temperature was raised to 150±10° C., and 406 parts by weight of propylene oxide was added dropwise successively while keeping the pressure at 4 to 6.5 kPa. It took one hour to complete the dropwise addition, and two hours for the pressure to be fully reduced. Subsequently, 0.8 parts by weight of potassium hydroxide was added, and then 32 parts by weight of propylene oxide was added dropwise successively. It took 0.5 hours to complete the dropwise addition, and 0.5 hours for the pressure to be fully reduced. Then, 26 parts by weight of ethylene oxide was added dropwise successively. It took 0.5 hours to complete the dropwise addition, and 0.5 hours for the pressure to be fully reduced. Thereafter, 10 parts by weight of KYOWAAD 600 (available from Kyowa Chemical Industry Co., Ltd.) was added to perform adsorption treatment at 95° C. for one hour, followed by filtration, whereby alkali metal was removed. The contents of the autoclave was cooled to 60° C. and taken out, whereby, 500 parts by weight of an alkylene oxide adduct was obtained. This adduct is taken as an ester compound of glutamic acid of a N-PO 6 mol EO 2 mol block adduct and di-PO 34 mol EO 4 mol block adduct (A-5).

Production Example 6

Production of Pentaerythritol BO 60 mol Adduct (A-6)

A 1-L autoclave equipped with a stirrer, a thermometer, a manometer, a pressure-resistant dropping funnel, and vacuum and nitrogen-introducing lines was charged with 14 parts by weight of pentaerythritol (I) [molecular weight: 136, product name: Pentarit (available from Koei Chemical Co., Ltd.)] and 0.8 parts by weight of potassium hydroxide, and stirring was started. Nitrogen was injected and the temperature was raised to 90° C. Then, the pressure was reduced to 0.005 MPa, and stirring was performed for one hour. Subsequently, the temperature was raised to 130±10° C., and 432 parts by weight of butylene oxide was added dropwise successively while keeping the pressure at 4 to 6.5 kPa. It took one hour to complete the dropwise addition, and two hours for the pressure to be fully reduced. Thereafter, 10 parts by weight of KYOWAAD 600 (available from Kyowa Chemical Industry Co., Ltd.) was added to perform adsorption treatment at 95° C. for one hour, followed by filtration, whereby alkali metal was removed. The contents of the autoclave was cooled to 60° C. and taken out, whereby 400 parts by weight of an alkylene oxide adduct was obtained. This adduct is taken as a pentaerythritol BO 60 mol adduct (A-6).

Production Example 7

Production of Pentaerythritol BO 80 mol EO 12 mol Block Adduct (A-7)

An amount of 400 parts by weight of the pentaerythritol BO 60 mol adduct (A-6) obtained in Production Example 6 was heated to 130±10° C., and 129 parts by weight of butylene oxide was added dropwise successively while keeping the pressure at 4 to 6.5 kPa. It took 0.5 hours to complete the dropwise addition, and 0.5 hours for the pressure to be fully reduced. Subsequently 47 parts by weight of ethylene oxide was added dropwise successively. It took 0.5 hours to complete the dropwise addition, and 0.5 hours for the pressure to be fully reduced. Thereafter, 10 parts by weight of KYOWAAD 600 (available from Kyowa Chemical Industry Co., Ltd.) was added to perform adsorption treatment at 95° C. for one hour, followed by filtration, whereby alkali metal was removed. The contents of the autoclave was cooled to 60° C. and taken out, whereby 500 parts by weight of an alkylene oxide adduct was obtained. This adduct is taken as a pentaerythritol BO 80 mol EO 12 mol block adduct (A-7).

Production Example 8

Production of Trimethylolpropane PO 60 mol Adduct (A-8)

A 1-L autoclave equipped with a stirrer, a thermometer, a manometer, a pressure-resistant dropping funnel, and vacuum and nitrogen-introducing lines was charged with 14 parts by weight of trimethylolpropane (I) [molecular weight: 134, product name: Trimethylolpropane (available from Bayer Chemicals)] and 0.8 parts by weight of potassium hydroxide, and stirring was started. Nitrogen was injected and the temperature was raised to 90° C. Then, the pressure was reduced to 0.005 MPa, and stirring was performed for one hour. Subsequently, the temperature was raised to 130±10° C., and 348 parts by weight of propylene oxide was added dropwise successively while keeping the pressure at 4 to 6.5 kPa. It took one hour to complete the dropwise addition, and two hours for the pressure to be fully reduced. Thereafter, 10 parts by weight of KYOWAAD 600 (available from Kyowa Chemical Industry Co., Ltd.) was added to perform adsorption treatment at 95° C. for one hour, followed by filtration, whereby alkali metal was removed. The contents of the autoclave was cooled to 60° C. and taken out, whereby 350 parts by weight of an alkylene oxide adduct was obtained. This adduct is taken as a trimethylolpropane PO 60 mol adduct (A-8).

Examples 1 to 17 and Comparative Examples 1 to 6

Components in the amounts (parts by weight) shown in Tables 1 and 2 were stirred at 40° C. for 30 minutes to produce water permeability-imparting agents (Examples 1 to 17 and Comparative Examples 1 to 6).

Each of the obtained water permeability-imparting agents of Examples 1 to 16 and Comparative Examples 1 to 6 was diluted with 25° C. warm water to a nonvolatile component content of 0.5% by weight, whereby a diluted solution of the water permeability-imparting agent was obtained. A polypropylene spun bond non-woven fabric (weight per unit area: 18 g/m$^2$) was lubricated with the diluted solution of the water permeability-imparting agent in an amount of 0.5%. In this lubrication, the non-woven fabric was immersed into the diluted solution of the water permeability-imparting agent in a lubricating bath, then squeezed through a mangle (pickup: 100%). The non-woven fabric was then dried with a wind-circulation dryer at 80° C. for 30 minutes, and left to stand at room temperature for eight hours or longer for drying. Thus, a water permeable non-woven fabric was obtained. The obtained non-woven fabric was evaluated for properties (the amount of the water permeability-imparting agent attached, the initial water permeability of the non-woven fabric, the repetition water permeability of the non-woven fabric, the liquid permeability, and the rewet prevention performance) by the following evaluation method. Table 1 and Table 2 show the results.

For the obtained water permeability-imparting agent of Example 17, the evaluation was performed in the same manner as in Examples 1 to 16 except that the "nonvolatile component content of 0.5% by weight" was changed to "nonvolatile component content of 1.0% by weight". Table 2 shows the results.

The abbreviations in Table 1 and Table 2 are as follows.
(A-1): pentaerythritol PO 120 mol adduct (m=30, n=0, n/m=0, l=4)
(A-2): pentaerythritol PO 120 mol EO 10 mol block adduct (m=30, n=2.5, n/m=0.083, l=4)
(A-3): trimethylolpropane PO 70 mol EO 20 mol block adduct (m=23.3, n=6.7, n/m=0.28, l=3)
(A-4): trimethylolpropane PO 60 mol EO 6 mol random adduct EO 6 mol block adduct (m=22, n=2, n/m=0.091, l=3)
(A-5): ester compound (m=24.7, n=3.3, n/m=0.13, l=3) of glutamic acid of a N-PO 6 mol EO 2 mol block adduct and di-PO 34 mol EO 4 mol block adduct
(A-6): pentaerythritol BO 60 mol adduct (m=15, n=0, n/m=0, l=4)
(A-7): pentaerythritol BO 80 mol EO 12 mol block adduct (m=20, n=3, n/m=0.15, l=4)
(A-8): trimethylolpropane PO 60 mol adduct (m=20, n=0, n/m=0, l=3)
(A'-1): pentaerythritol PO 120 mol EO 70 mol block adduct (m=30, n=17.5, n/m=0.58, l=4)
(A'-2): trimethylolpropane PO 20 mol EO 40 mol block adduct (m=6.7, n=13.3, n/m=2.0, l=3)
(A'-3): trimethylolpropane PO 21 mol EO 3 mol random adduct EO 15 mol block adduct (m=8, n=5, n/m=0.63, l=3)
(A'-4): oleyl alcohol PO 70 mol EO 20 mol block adduct (m=70, n=20, n/m=0.28, l=1)
(B-1): sodium di(2-ethylhexyl)sulfosuccinate
(B-2): sodium didodecyl sulfosuccinate
(B-3): potassium 1-octyl-2-hexadecyl sulfosuccinate
(B'-1): sodium hexadecylcarboxylate
(C-1): isodecanol EO 5 mol adduct
(C-2): octadecyl alcohol EO 5 mol adduct
(C-3): hardened castor oil EO 20 mol adduct trioleate
(C-4): polyester (number average molecular weight: 6000) of a hardened castor oil EO 25 mol adduct, maleic acid, and stearic acid,
(C-5): hardened castor oil EO 43 mol adduct
(C-6): polyoxyethylene (number average molecular weight: 400) dioleate

[Evaluation Method]
(1) Amount of Water Permeability-Imparting Agent Attached

The water-permeable non-woven fabric was conditioned at a temperature of 25° C. and a humidity of 40% RH for 24 hours. Immediately after the conditioning, the fabric was subjected to extraction with a rapid residual fat extraction apparatus model R-11 (Tokai Keiki K.K.) using methanol/n-hexane. The extract was put in an aluminum cup. The aluminum cup was placed on an explosion-proof hot plate at about 100° C. to completely remove the solvent, and the weight of the water permeability-imparting agent was measured. The amount C (% by weight) of the nonvolatile component of the water permeability-imparting agent attached was determined by the following formula. The larger is the amount of the water permeability-imparting agent attached to the water-permeable non-woven fabric, the better is the attaching ability to the water permeable non-woven fabric.

$$C\ (\%\ \text{by weight}) = W2/W1 \times 100$$

W1: The weight (g) of the water-permeable non-woven fabric immediately after conditioning
W2: The weight (g) of the water permeability-imparting agent in the extract (2) Initial Water Permeability of Non-Woven Fabric The non-woven fabric is placed on filter paper (Toyo Roshi Kaisha, Ltd., No. 5). One drop (about 0.05 mL) of saline is added dropwise from a burette set at a height of 10 mm high from the surface of the non-woven fabric. The time for the drop to disappear from the surface of the non-woven fabric is measured. Twenty dots are put on the surface of the non-woven fabric with a marking pen, and the measurement is performed at the 20 points. The number of dots at which the saline disappears in less than five seconds is shown. In cases where this number is 18 or greater, the non-woven fabric has excellent initial water permeability.

(3) Repetition Water Permeability of Non-Woven Fabric

Twenty dots are put on the surface of the non-woven fabric with a marking pen in accordance with the method for testing the initial water permeability of the non-woven fabric. The time for the saline to disappear is measured at the 20 points, and the number of dots at which the saline disappears in less than five seconds is shown. This operation is repeated on the tested non-woven fabric. In this repetition test, the larger is the disappearing number (the number of points at which the time for saline to disappear is less than 5 seconds) after repeated operations, the better is the repetition water permeability of the non-woven fabric.

(4) Liquid Permeability

First measurement: A test non-woven fabric (10 cm×10 cm) is placed on filter paper (available from ADVANTEC, No. 424 (10 cm×10 cm)), and 5 mL of saline (NaCl solution) is passed through the fabric. The liquid strike-through time is measured.

Second and third measurements: The above procedure is conducted twice at a one-minute interval, and the liquid strike-through time is measured.

The shorter the liquid strike-through time is, the higher the liquid permeation rate is and the better the liquid permeability is.

(5) Rewet Prevention Performance

The non-woven fabric (10 cm×10 cm) is placed on a commercially available disposable diaper. On the non-woven fabric is further placed a cylinder with an inner diameter of 60 mm. Saline (100 mL) is poured into the cylinder and absorbed into the disposable diaper through the non-woven fabric. When all the saline is absorbed into the disposable diaper, the cylinder is removed. Preliminarily weighed 20 sheets of filter paper (available from Toyo Roshi Kaisha, Ltd., No. 5) are placed on the disposable diaper, and a 5-kg weight is put on the sheets. After five-minute standing, the weight of the filter paper is measured, and the increment of the weight is determined as the rewet amount (g). A rewet amount of 1.2 g or less is regarded acceptable. A rewet amount (g) of 1.0 g or less indicates excellent rewet prevention performance.

TABLE 1

|  |  |  | Solubility parameter (cal/cm³)$^{1/2}$ | HLB | Example |  |  |  |  |  |  |  |  |  |  |
|---|---|---|---|---|---|---|---|---|---|---|---|---|---|---|---|---|
|  |  |  |  |  | 1 | 2 | 3 | 4 | 5 | 6 | 7 | 8 | 9 | 10 | 11 |
| Water permeability-imparting agent | Alkylene oxide adduct (A) of polyvalent active hydrogen compound represented by Formula (1) | (A-1) | 8.7 | 4.1 | 100 | — | 20 | — | — | 20 | — | 10 | — | 30 | 50 |
|  |  | (A-2) | 8.7 | 5.0 | — | 50 | — | 60 | 30 | — | 40 | — | — | — | — |
|  |  | (A-3) | 8.8 | 6.7 | — | — | — | 20 | — | — | — | — | 40 | — | — |
|  |  | (A-4) | 8.7 | 5.1 | — | — | — | — | — | — | — | — | — | — | — |
|  |  | (A-5) | 8.9 | 6.2 | — | — | — | — | — | — | — | — | — | — | — |
|  |  | (A-6) | 9.0 | 2.6 | — | — | — | — | — | — | — | — | — | — | — |
|  |  | (A-7) | 9.1 | 3.7 | — | — | — | — | — | — | — | — | — | — | — |
|  |  | (A-8) | 8.7 | 4.1 | — | — | — | — | — | — | — | — | — | — | — |
|  |  | (A'-1) | 8.9 | 6.1 | — | — | — | — | — | — | — | — | — | — | — |
|  |  | (A'-2) | 9.1 | 12.8 | — | — | — | — | — | — | — | — | — | — | — |
|  |  | (A'-3) | 8.9 | 10.3 | — | — | — | — | — | — | — | — | — | — | — |
|  |  | (A'-4) | 8.8 | 6.3 | — | — | — | — | — | — | — | — | — | — | — |
|  | Anionic surfactant (B) | (B-1) | — | — | — | 50 | 20 | — | — | — | — | — | — | 40 | — |
|  |  | (B-2) | — | — | — | — | — | — | 30 | 10 | — | — | — | — | 20 |
|  |  | (B-3) | — | — | — | — | 40 | — | — | 20 | — | — | 30 | — | — |
|  |  | (B'-1) | — | — | — | — | — | — | — | — | — | — | — | — | — |
|  | Nonionic surfactant (C) other than (A) | (C-1) | — | — | — | — | 20 | — | — | 20 | — | — | — | — | — |
|  |  | (C-2) | — | — | — | — | — | 20 | 20 | — | — | — | — | — | — |
|  |  | (C-3) | — | — | — | — | — | — | — | 30 | — | 40 | — | 20 | — |
|  |  | (C-4) | — | — | — | — | — | — | — | — | 20 | 30 | 20 | 10 | — |
|  |  | (C-5) | — | — | — | — | — | — | — | — | 20 | — | 20 | 10 | — |
|  |  | (C-6) | — | — | — | — | — | — | — | 20 | — | 20 | — | — | 30 |
|  | Total |  | — | — | 100 | 100 | 100 | 100 | 100 | 100 | 100 | 100 | 100 | 100 | 100 |
| Evaluation items | The amount of nonvolatile component of the water permeability-imparting agent attached (% by weight) |  | — | — | 0.5 | 0.5 | 0.5 | 0.5 | 0.5 | 0.5 | 0.5 | 0.5 | 0.5 | 0.5 | 0.5 |

TABLE 1-continued

| | | Solubility parameter (cal/cm³)^(1/2) | HLB | Example 1 | 2 | 3 | 4 | 5 | 6 | 7 | 8 | 9 | 10 | 11 |
|---|---|---|---|---|---|---|---|---|---|---|---|---|---|---|
| Initial water permeability (points) | | — | — | 19 | 20 | 20 | 19 | 20 | 20 | 19 | 20 | 20 | 20 | 20 |
| Repetition water permeability (points) | First | — | — | 19 | 20 | 20 | 19 | 20 | 20 | 19 | 20 | 20 | 20 | 20 |
| | Second | — | — | 19 | 20 | 20 | 19 | 20 | 20 | 19 | 20 | 20 | 20 | 20 |
| | Third | — | — | 19 | 20 | 19 | 19 | 19 | 20 | 18 | 20 | 20 | 20 | 20 |
| | Fourth | — | — | 18 | 19 | 15 | 17 | 17 | 19 | 14 | 20 | 19 | 20 | 20 |
| | Fifth | — | — | 17 | 18 | 13 | 16 | 14 | 18 | 13 | 19 | 18 | 18 | 20 |
| Liquid permeability (seconds) | First | — | — | 12.7 | 11.7 | 9.4 | 12.4 | 11.9 | 11.6 | 11.8 | 11.4 | 12.5 | 11.2 | 12.1 |
| | Second | — | — | 13.6 | 13.7 | 13.5 | 13.1 | 14.1 | 12.2 | 13.2 | 12.5 | 12.9 | 11.9 | 12.6 |
| | Third | — | — | 13.9 | 14.5 | 15.2 | 14.4 | 14.2 | 14.8 | 14.2 | 13.7 | 13.1 | 12.4 | 12.8 |
| Rewet prevention performance (g) | | — | — | 1.0 | 0.9 | 1.0 | 0.9 | 1.0 | 1.0 | 0.8 | 1.0 | 1.0 | 0.9 | 0.9 |

| | | | Solubility parameter (cal/cm³)^(1/2) | HLB | Example 12 | 13 | 14 | 15 | 16 | 17 | Comparative Example 1 | 2 | 3 | 4 | 5 | 6 |
|---|---|---|---|---|---|---|---|---|---|---|---|---|---|---|---|---|
| Water permeability-imparting agent | Alkylene oxide adduct (A) of polyvalent active hydrogen compound represented by Formula (1) | (A-1) | 8.7 | 4.1 | — | — | — | — | — | — | — | — | — | — | — | — |
| | | (A-2) | 8.7 | 5.0 | — | — | — | — | — | — | — | — | — | — | — | — |
| | | (A-3) | 8.8 | 6.7 | — | — | — | — | — | — | — | — | — | — | — | — |
| | | (A-4) | 8.7 | 5.1 | 50 | — | — | — | — | — | — | — | — | — | — | — |
| | | (A-5) | 8.9 | 6.2 | — | 50 | — | — | — | — | — | — | — | — | — | — |
| | | (A-6) | 9.0 | 2.6 | — | — | 30 | — | — | — | — | — | — | — | — | — |
| | | (A-7) | 9.1 | 3.7 | — | — | — | 40 | — | — | — | — | — | — | — | — |
| | | (A-8) | 8.7 | 4.1 | — | — | — | — | 40 | 40 | — | — | — | — | — | — |
| | | (A'-1) | 8.9 | 6.1 | — | — | — | — | — | — | — | 40 | 20 | — | — | — |
| | | (A'-2) | 9.1 | 12.8 | — | — | — | — | — | — | 40 | — | 20 | — | — | — |
| | | (A'-3) | 8.9 | 10.3 | — | — | — | — | — | — | — | — | — | — | 50 | — |
| | | (A'-4) | 8.8 | 6.3 | — | — | — | — | — | — | — | — | — | — | — | 40 |
| Anionic surfactant (B) | | (B-1) | — | — | — | 15 | — | — | 15 | 15 | 20 | — | — | 30 | 30 | — |
| | | (B-2) | — | — | 30 | — | 20 | — | — | — | — | 40 | — | — | 10 | 20 |
| | | (B-3) | — | — | — | 15 | — | 20 | — | — | — | — | — | — | — | — |
| | | (B'-1) | — | — | — | — | 20 | 20 | 15 | 15 | — | — | — | 50 | — | — |
| Nonionic surfactant (C) other than (A) | | (C-1) | — | — | 10 | — | — | 10 | — | — | — | — | — | — | — | — |
| | | (C-2) | — | — | — | 10 | — | — | 10 | 10 | — | 20 | 20 | 20 | — | — |
| | | (C-3) | — | — | — | — | 15 | 10 | — | — | — | — | 40 | — | — | 40 |
| | | (C-4) | — | — | — | 10 | — | — | 10 | 10 | — | — | — | — | 10 | — |
| | | (C-5) | — | — | 10 | — | — | — | 10 | 10 | — | 20 | — | — | — | — |
| | | (C-6) | — | — | — | — | 15 | — | — | — | — | 20 | — | — | — | — |
| | Total | | — | — | 100 | 100 | 100 | 100 | 100 | 100 | 100 | 100 | 100 | 100 | 100 | 100 |
| Evaluation items | The amount of nonvolatile component of the water permeability-imparting agent attached (% by weight) | | — | — | 0.5 | 0.5 | 0.5 | 0.5 | 0.5 | 1.0 | 0.5 | 0.5 | 0.5 | 0.5 | 0.5 | 0.5 |
| | Initial water permeability (points) | | — | — | 20 | 19 | 19 | 20 | 19 | 20 | 12 | 17 | 17 | 15 | 15 | 18 |
| | Repetition water permeability (points) | First | — | — | 20 | 19 | 19 | 20 | 19 | 20 | 12 | 17 | 17 | 15 | 15 | 18 |
| | | Second | — | — | 19 | 18 | 19 | 20 | 18 | 20 | 10 | 15 | 12 | 1 | 17 | 3 |
| | | Third | — | — | 19 | 18 | 19 | 20 | 18 | 20 | 9 | 13 | 8 | 0 | 13 | 1 |
| | | Fourth | — | — | 18 | 16 | 17 | 18 | 18 | 20 | 6 | 7 | 5 | 0 | 10 | 0 |
| | | Fifth | — | — | 15 | 14 | 14 | 15 | 16 | 19 | 2 | 3 | 0 | 0 | 8 | 0 |
| | Liquid permeability (seconds) | First | — | — | 11.5 | 11.9 | 12.4 | 11.3 | 12.0 | 11.3 | 14.5 | 12.4 | 11.8 | 10.7 | 13.1 | 12.2 |
| | | Second | — | — | 12.1 | 13.2 | 12.9 | 13.5 | 12.8 | 11.8 | 15.8 | 18.9 | 19.5 | 17.2 | 16.5 | 15.4 |
| | | Third | — | — | 14.1 | 13.9 | 13.6 | 13.8 | 13.7 | 12.9 | 17.4 | 20.2 | 19.9 | 18.9 | 20.7 | 18.4 |
| | Rewet prevention performance (g) | | — | — | 1.0 | 0.8 | 0.9 | 0.8 | 0.9 | 1.0 | 1.5 | 1.5 | 1.2 | 2.0 | 2.0 | 1.5 |

The results shown in Table 1 and Table 2 clearly show that the water permeability-imparting agents of Examples 1 to 17 gave the non-woven fabrics excellent initial water permeability and repetition water permeability, as well as good rewet prevention performance.

In contrast, both the initial water permeability and the repetition water permeability were poor in the water permeability-imparting agents of Comparative Examples 1 to 3, 5, and 6, in which the alkylene oxide adduct (A) of a polyvalent active hydrogen compound represented by Formula (1) was out of the range of the present application, and in the water permeability-imparting agent of Comparative Example 4, which did not contain the alkylene oxide adduct (A) of a polyvalent active hydrogen compound represented by Formula (1). Additionally, the rewet prevention performance was also poor in the water permeability-imparting agents of Comparative Examples 1 to 6.

INDUSTRIAL APPLICABILITY

The water-permeable fibers of the present invention and the non-woven fabric containing the fibers are suitably used as a surface material of a water-absorbing article, in particular a surface material of a hygienic material such as a disposable diaper or a sanitary product (e.g., sanitary napkin).

The water-permeable fibers of the present invention and the non-woven fabric containing the fibers are also usable in a second sheet, a water-absorbing body, an industrial or medical wiper, an absorbing pad, a water-permeable sheet, and the like.

The invention claimed is:

1. A water permeability-imparting agent comprising:
an alkylene oxide adduct (A) of a polyvalent active hydrogen compound represented by Formula (1):

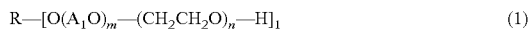  (1)

wherein R represents a residue, after removal of all active hydrogen, of the polyvalent active hydrogen compound; $A^1O$ represents a C3 or C4 alkyleneoxy group; m represents an average addition mole number of $A^1O$ and is a number of 4 to 50; n represents an average addition mole number of $CH_2CH_2O$; and l represents a valence and is an integer of 3 to 6,
an average addition mole number ratio between $A^1O$ and $CH_2CH_2O$ in Formula (1), n/m, being 0 to 0.5, and
the alkylene oxide adduct (A) of a polyvalent active hydrogen compound represented by Formula (1) is contained in an amount of 10 to 80% by weight based on the weight of the water permeability-imparting agent.

2. The water permeability-imparting agent according to claim 1,
wherein in Formula (1), n is a number of 0 to 15.

3. The water permeability-imparting agent according to claim 1,
wherein the alkylene oxide adduct (A) of a polyvalent active hydrogen compound represented by Formula (1) has a solubility parameter of 8.5 to 9.5 $(cal/cm^3)^{1/2}$.

4. The water permeability-imparting agent according to claim 1,
wherein the polyvalent active hydrogen compound is glycerol, trimethylolpropane, pentaerythritol, sorbitan, sorbitol, glutamic acid, castor oil, or hardened castor oil.

5. The water permeability-imparting agent according to claim 1, further comprising:
an anionic surfactant (B); and/or
a nonionic surfactant (C) other than the alkylene oxide adduct (A) of a polyvalent active hydrogen compound represented by Formula (1).

6. The water permeability-imparting agent according to claim 5,
wherein the anionic surfactant (B) is a dialkyl sulfosuccinate.

7. The water permeability-imparting agent according to claim 5,
wherein the nonionic surfactant (C) is a monohydric alcohol nonionic surfactant and/or a polyol nonionic surfactant.

8. The water permeability-imparting agent according to claim 5, containing 10 to 80% by weight of the alkylene oxide adduct (A) of a polyvalent active hydrogen compound represented by Formula (1), 40% by weight or less of the anionic surfactant (B), and 50% by weight or less of the nonionic surfactant (C) other than (A), based on the weight of the water permeability-imparting agent.

9. Water-permeable fibers comprising:
hydrophobic fibers; and
a nonvolatile component of the water permeability-imparting agent according to claim 1 attached to the hydrophobic fibers,
the nonvolatile component being attached in an amount of 0.05 to 2% by weight based on the weight of the hydrophobic fibers.

10. A non-woven fabric comprising:
the water-permeable fibers according to claim 9.

11. A water-absorbing article comprising:
a surface material containing the non-woven fabric according to claim 10.

* * * * *